US009434672B2

(12) United States Patent
Frey et al.

(10) Patent No.: US 9,434,672 B2
(45) Date of Patent: *Sep. 6, 2016

(54) METHOD FOR PRODUCING ISONONANOIC ACIDS FROM 2-ETHYL HEXANOL

(71) Applicant: Oxea GmbH, Oberhausen (DE)

(72) Inventors: Guido D. Frey, Riedstadt (DE); Matthias Eisenacher, Wesel (DE); Kristina Kockrick, Düsseldorf (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/413,503

(22) PCT Filed: Jun. 18, 2013

(86) PCT No.: PCT/EP2013/001798
§ 371 (c)(1),
(2) Date: Jan. 8, 2015

(87) PCT Pub. No.: WO2014/008975
PCT Pub. Date: Jan. 16, 2014

(65) Prior Publication Data
US 2015/0191410 A1    Jul. 9, 2015

(30) Foreign Application Priority Data
Jul. 13, 2012 (DE) .......................... 10 2012 013 969

(51) Int. Cl.
C07C 51/235 (2006.01)
C07C 1/24 (2006.01)
C07C 45/50 (2006.01)
C07C 51/56 (2006.01)
C07C 51/60 (2006.01)
C07C 53/126 (2006.01)
C07C 67/04 (2006.01)
C07C 67/08 (2006.01)
C07C 67/10 (2006.01)
C07C 231/02 (2006.01)
C07D 301/30 (2006.01)

(52) U.S. Cl.
CPC .............. *C07C 51/235* (2013.01); *C07C 1/24* (2013.01); *C07C 45/50* (2013.01); *C07C 51/56* (2013.01); *C07C 51/60* (2013.01); *C07C 53/126* (2013.01); *C07C 67/04* (2013.01); *C07C 67/08* (2013.01); *C07C 67/10* (2013.01); *C07C 231/02* (2013.01); *C07D 301/30* (2013.01); *C07C 2521/04* (2013.01)

(58) Field of Classification Search
CPC ......... C07C 67/08; C07C 1/24; C07C 45/50; C07C 51/235; C07C 11/02; C07C 47/02; C07C 53/126; C07C 69/28; C07C 69/30; C07C 69/33; C07C 2521/04; C07C 29/48; C08K 5/10; C08K 5/103; C10M 129/70; C10M 129/74; C10M 2207/281; C10M 2207/283

USPC .......... 106/505; 508/463; 524/315; 560/174
See application file for complete search history.

(56) References Cited

U.S. PATENT DOCUMENTS

| 2,919,973 | A | 1/1960 | Stillwell et al. |
| 3,527,809 | A | 9/1970 | Pruett et al. |
| 4,148,830 | A | 4/1979 | Pruett et al. |
| 4,247,486 | A | 1/1981 | Brewester et al. |
| 4,283,562 | A | 8/1981 | Billig et al. |
| 6,228,820 | B1 | 5/2001 | Sakei et al. |
| 6,433,217 | B1 | 8/2002 | Rosenbrand et al. |
| 6,617,289 | B2 | 9/2003 | Memita et al. |
| 7,799,945 | B2 | 9/2010 | Springer |
| 2003/0078453 | A1* | 4/2003 | Springer ............... C07C 51/235 562/534 |
| 2004/0238787 | A1* | 12/2004 | Wiese ..................... C07C 69/80 252/182.28 |
| 2011/0021790 | A1 | 1/2011 | Katz et al. |
| 2011/0087046 | A1* | 4/2011 | Frey ........................ C07C 67/08 560/183 |
| 2015/0158805 | A1* | 6/2015 | Frey ........................ C08K 5/103 508/463 |
| 2015/0166456 | A1* | 6/2015 | Johnen .................... C07C 67/04 525/451 |

FOREIGN PATENT DOCUMENTS

| CA | 1081254 A1 | 7/1980 |
| DE | 950007 C | 10/1956 |
| DE | 2604545 A1 | 8/1977 |
| DE | 2844638 A1 | 4/1980 |
| DE | 19906518 A1 | 8/2000 |
| DE | 19908320 A1 | 8/2000 |
| DE | 10010771 C1 | 5/2001 |
| DE | 102009048771 A1 | 4/2011 |

(Continued)

OTHER PUBLICATIONS

International Preliminary Report on Patentability dated Jan. 22, 2015.
International Search Report dated Oct. 10, 2013.
Scharfe, G., "Convert butenes to high octane oligomers", Hydrocarbon Processing, Apr. 1973, pp. 171-173.
G. Hübner, "Vinylierung hoherer Carbonsauren an Katalysatorschmelzen", Fette, Seifen, Anstrichmittel, 1966, pp. 290-292, 68, 4.

(Continued)

*Primary Examiner* — Jafar Parsa
*Assistant Examiner* — Amy C Bonaparte
(74) *Attorney, Agent, or Firm* — Michael W. Ferrell

(57) ABSTRACT

Process for preparing isononanoic acid proceeding from 2-ethylhexanol, characterized in that (a) 2-ethylhexanol is dehydrated to octene in the presence of a catalyst; (b) the octene obtained in step a) is reacted in the presence of a transition metal compound of group VIII of the periodic table of the elements with carbon monoxide and hydrogen to give isononanal; and (c) the isononanal obtained in step b) is oxidized to isononanoic acid.

19 Claims, No Drawings

(56) References Cited

FOREIGN PATENT DOCUMENTS

| | | |
|---|---|---|
| EP | 0475751 A1 | 3/1992 |
| EP | 0497340 A2 | 8/1992 |
| EP | 0903335 A1 | 3/1999 |
| EP | 1057525 A2 | 12/2000 |
| EP | 1199300 A2 | 4/2002 |
| EP | 1281701 A1 | 2/2003 |
| EP | 1854778 A1 | 11/2007 |
| GB | 313426 A | 6/1929 |
| GB | 2033387 A | 5/1980 |
| WO | 9012849 A1 | 11/1990 |
| WO | 03029180 A1 | 4/2003 |
| WO | 2011139360 A1 | 11/2011 |

OTHER PUBLICATIONS

Robert L. Adelman, "The Interchange Reaction of Vinyl Acetate With Organic Acids", Journal Organic Chemistry, 1949, pp. 1057-1077, 14.

R.H. Friedlander et al., "Make Plasticizer Olefins Via N-Butene Dimerization", Hydrocarbon Processing, Feb. 1986, pp. 31-33.

* cited by examiner

METHOD FOR PRODUCING ISONONANOIC ACIDS FROM 2-ETHYL HEXANOL

CLAIM FOR PRIORITY

This application is a national phase application of PCT/EP2013/001798 FILED Jun. 18, 2013 which was based on application DE 10 2012 013 969.1 FILED Jul. 13, 2012. The priorities of PCT/EP2013/001798 and DE 10 2012 013 969.1 are hereby claimed and their disclosures incorporated herein by reference.

TECHNICAL FIELD

The present invention relates to isononanoic acid proceeding from 2-ethylhexanol, to the preparation thereof by dehydration of 2-ethylhexanol, hydroformylation of the octene obtained to isononanal and subsequent oxidation to the corresponding isononanoic acid, and to the preparation of vinyl isononanoate, the glycidyl ester, carboxylates, isononanoyl halides, isononanoic anhydrides and isononanamides proceeding from said isononanoic acid prepared in this way.

BACKGROUND

Isononanoic acid, a mixture of structurally branched C9-monocarboxylic acids, is an important intermediate in industrial organic chemistry which is processed to give a multitude of conversion products for a wide variety of different fields of use. For example, the salts thereof are used as drying accelerators or siccatives for coatings, and the esters thereof with ethylene glycols serve as plasticizers for PVC or for polyvinyl butyral films and as coalescence agents in aqueous dispersions of polymers (Weissermel, Arpe, Industrielle Organische Chemie, VCH Verlagsgesellschaft, 3rd edition, 1988, p. 145; DE 10 2009 048 771 A1). The esterification of isononanoic acid with polyols such as neopentyl glycol, trimethylolpropane, ditrimethylolpropane, pentaerythritol or dipentaerythritol gives lubricant esters which are used in the operation of refrigerators. Isononanoic acid is frequently esterified in a mixture with other C4-C12-monocarboxylic acids such as 2-methylbutyric acid, n-pentanoic acid, n-heptanoic acid, 2-ethylhexanoic acid or n-octanoic acid. (EP 1 281 701 A1; EP 1 199 300 A2; EP 0 903 335 A1; WO90/12849 A1; EP 0 475 751 A1).

In addition, isononanoic acid is converted to the corresponding vinyl ester which, as a comonomer, modifies the properties of polymers such as polyvinyl acetate, polyvinyl chloride, polystyrene or polyacrylic esters. The corresponding copolymers can be processed to give paints which feature improved hydrolysis resistance and relatively low moisture absorption. Vinyl esters can be prepared by reaction of the isononanoic acids with acetylene, preferably in the presence of zinc salts at temperatures of 200-230° C. (G. Hübner, Fette, Seifen, Anstrichmittel 68, 290 (1966); Ullmann's Encyclopedia of Industrial Chemistry, 7th Edition, 2011, Wiley, Volume 38, pages 107-124; EP 1 057 525 A2), or by what is called the transvinylation reaction with an vinyl ester of another carboxylic acid, frequently vinyl acetate or vinyl propionate, in the presence of transition metal catalysts (Ullmann's Encyclopedia of Industrial Chemistry, 7th Edition, 2011, Wiley, Volume 38, pages 107-124; Adelmann, Journal Organic Chemistry, 1949, 14, pages 1057-1077; DE 199 08 320 A1, EP 0 497 340 A2, WO2011/139360 A1, WO2011/139361 A1).

The raw material used for the industrial preparation of isononanoic acid is the C4 cut from the steamcracking of naphtha. The availability thereof compared to the C2 and C3 cracking products can be controlled by the conditions of steamcracking and is guided by the market conditions.

1,3-Butadiene is first removed from the C4 cracking products by extraction or by selective hydrogenation to n-butenes. The resulting C4 raffinate, also called raffinate I, comprises predominantly the unsaturated butenes isobutene, 1-butene and 2-butene, and the hydrogenated products n-butane and isobutane. Isobutene is removed from the raffinate I in the next step, and the resulting isobutene-free C4 mixture is referred to as raffinate II.

For the isobutene removal, various processes are employed in industrial production, in which the highest reactivity of the isobutene in relative terms in the raffinate I is exploited. A known method is the reversible proton-catalysed addition of water to give tert-butanol, or methanol addition to give methyl tert-butyl ether. Isobutene can be recovered again from these addition products by redissociation (Weissermel, Arpe, Industrielle Organische Chemie [Industrial Organic Chemistry], VCH Verlagsgesellschaft, 3rd Edition, 1988, pages 74-79).

It is likewise possible to contact the butadiene-free C4 raffinate at elevated temperature and under pressure with an acidic suspended ion exchanger. Isobutene oligomerizes to diisobutene, triisobutene, and in a small portion to higher oligomers. The oligomers are separated from the unreacted C4 compounds. It is then possible to obtain diisobutene or triisobutene in pure form by distillation from the oligomer. The dimerization of n-butenes with isobutene forms co-dimer to a small degree (Weissermel, Arpe, Industrielle Organische Chemie, VCH Verlagsgesellschaft, 3rd Edition, 1988, p. 77; Hydrocarbon Processing, April 1973, pages 171-173).

Diisobutene, either prepared by the oligomerization of pure isobutene obtained by redissociation or obtained in the course of workup of a butadiene-free raffinate I, is then converted to a C9 derivative lengthened by one carbon atom. Industrial operation involves the hydroformylation or oxo process in which diisobutene is converted to the corresponding aldehyde with carbon monoxide and hydrogen in the presence of rhodium or cobalt catalysts. Since diisobutene predominantly comprises the octenes 2,4,4-trimethyl-1-pentene and 2,4,4-trimethyl-2-pentene, the hydroformylation reaction gives the C9 aldehyde 3,5,5-trimethylhexanal as the main constituent. Further C9 isomers present in small amounts are 3,4,4- and 3,4,5-trimethylhexanal, and also 2,5,5-trimethylhexanal, 4,5,5-trimethylhexanal and 6,6-dimethylheptanal. Oxidation of this aldehyde mixture gives an industrially available isononanoic acid typically having a content of 3,5,5-trimethylhexanoic acid of about 90% (Ullmanns Encyklopädie der technischen Chemie, 4th Edition, 1975, Verlag Chemie, Volume 9, pages 143-145; EP 1 854 778 A1).

Diisobutene can likewise be converted by what is called the hydrocarboxylation or Koch reaction with carbon monoxide and water in the presence of sulphuric acid to the highly branched isononanoic acid 2,2,4,4-tetramethyl-1-pentanoic acid. Owing to the double alkyl branch at the carbon atom adjacent to the carboxyl group, this isononanoic acid is frequently also referred to as neo-nonanoic acid (Ullmanns Encyklopädie der technischen Chemie, 4th Edition, 1975, Verlag Chemie, Volume 9, pages 143-145).

The n-butenes present in raffinate II after the isobutene removal are also converted industrially to butene oligomers, from which isomeric octenes are separated, and these are converted via the hydrocarboxylation to the corresponding isononanoic acids (DE 199 08 320 A1; DE 199 06 518 A1). The oligomerization of n-butenes is conducted industrially over acidic catalysts such as zeolites or phosphoric acid on supports. This gives octenes comprising dimethylhexenes as the main product. Further processes include the DIMERSOL process and the OCTOL process. The DIMERSOL process works with soluble nickel complex catalysts and leads to an octene mixture having a high proportion of 3- and 5-methylheptenes, in addition to dimethylhexenes and n-octenes. In the OCTOL process, supported fixed bed nickel catalysts are used and the resulting octene mixture features a low degree of branching (DE 199 08 320 A1, WO 03/029180 A1, Hydrocarbon Processing, February 1986, pages 31-33). According to DE 199 08 320 A1, the respective differently branched octene mixtures are converted via the hydrocarboxylation to the corresponding isononanoic acids, which are then converted to the corresponding vinyl esters. Vinyl esters of isononanoic acids based on an octene mixture from the OCTOL process are suitable as a plasticizing comonomer.

Against the background that the availability of octenes based on the C4 cut from naphtha cracking is limited and depends on the local conditions, it is desirable to develop further octene sources based on inexpensively available large-scale products which can be transported to various sites in a simple manner.

2-Ethylhexanol is available inexpensively as an industrial large-scale product which can be sold widely without any problems. As is well known, 2-ethylhexanol is prepared on the industrial scale by hydroformylation or oxo process using propylene to give n-butyraldehyde with subsequent alkali-catalysed aldol condensation to give 2-ethylhexenal followed by full hydrogenation to give 2-ethylhexanol (Ullmann's Encyclopedia of Industrial Chemistry, 7th Edition, 2011, Wiley, Volume 13, pages 579-584).

WO 03/029180 A1 briefly discusses the use of 2-ethylhexanol for preparation of an octene mixture which is processed via dehydration, hydroformylation and hydrogenation to give an isononanol mixture. The emphasis is on the adjustment of the viscosity of the isomeric dialkyl phthalates which are obtained by esterification of isomeric nonanols with phthalic acid or phthalic anhydride. No pointers are given to convert the dehydration products of 2-ethylhexanol to isononanoic acid.

The utilization of 2-ethylhexanol as the octene source enables the provision of isononanoic acid based on propylene, and reduces dependence on octene availability based on butene.

SUMMARY OF INVENTION

The present invention therefore consists in a process for preparing isononanoic acid proceeding from 2-ethylhexanol. The process is characterized in that
(a) 2-ethylhexanol is dehydrated to octene in the presence of a catalyst;
(b) the octene obtained in step a) is reacted in the presence of a transition metal compound of group VIII of the periodic table of the elements with carbon monoxide and hydrogen to give isononanal; and
(c) the isononanal obtained in step b) is oxidized to isononanoic acid.

The present invention likewise relates to isononanoic acid obtainable by
(a) dehydrating 2-ethylhexanol in the presence of a catalyst to octene;
(b) reacting the octene obtained in step a) in the presence of a transition metal compound of group VIII of the periodic table of the elements with carbon monoxide and hydrogen to give isononanal; and
(c) oxidizing the isononanal obtained in step b) to isononanoic acid.

DETAILED DESCRIPTION

The dehydration of 2-ethylhexanol can be performed either in the liquid phase or in the gas phase over a catalyst suitable therefor. Preference is given to dehydrating in the gas phase at temperatures in the range from 200 to 450° C., preferably from 250 to 380° C., using reactors customary in the art, in the presence of heterogeneous catalysts having dehydrating properties such as alumina in its various polymorphs, nickel precipitated on alumina, or phosphoric acid precipitated on silica or alumina. Such heterogeneous catalysts suitable for dehydration are known from the prior art (GB 313426, U.S. Pat. No. 2,468,764, U.S. Pat. No. 2,919,973) and are commercially available, for example, as Al3996 from BASF SE. U.S. Pat. No. 2,919,973 discusses the dehydration of 2-ethylhexanol over a heterogeneous alumina catalyst at temperatures around 350° C. and at a catalyst hourly space velocity of 2.4 to 2.8 liters of 2-ethylhexanol per liter of catalyst an hour. However, the prior art does not give any information regarding the isomer distribution in the octene mixture obtained.

The reactor used in the process according to the invention for the dehydration of 2-ethylhexanol may, as well as the catalyst bed, also contain further random packings or internals, for example Raschig rings, saddles, Pall rings, filter plates or column trays. If random packings are used, they are preferably positioned above the catalyst bed in order to reduce the dead volume. If dehydration is effected in the liquid phase, it is possible to dispense with stirrer apparatus, internals and random packings, such that only the dehydration catalyst is present in the reaction vessel. In a preferred mode of operation, 2-ethylhexanol is heated in an upstream vaporizer and conducted in gaseous form over the catalyst bed, optionally using an inert carrier gas such as nitrogen, carbon dioxide or noble gases. The space velocity V/Vh of the heterogeneous catalyst may vary over a wide range and is generally from 0.2 to 3.5 liters of 2-ethylhexanol per liter of catalyst and hour. The reaction mixture withdrawn from the dehydration zone is subsequently condensed. As a result of the water eliminated, an aqueous phase is obtained, which is separated from the organic olefin phase by simple phase separation. The octene obtained is a mixture of structurally isomeric octenes with the singly branched octenes 2-ethyl-1-hexene and cis/trans-3-methyl-3-heptene and cis/trans-3-methyl-2-heptene as main components. No significant amounts of di-C8-ethers are formed.

The octene present after removal of the splitting water is subsequently used without further purification, or appropriately after distillative purification, for the reaction with carbon monoxide and hydrogen in the hydroformylation reaction or oxo process. The mixture of carbon monoxide and hydrogen used is also referred to as synthesis gas. The hydroformylation reaction is performed in a homogeneous reaction system. The term "homogeneous reaction system" represents a homogeneous solution composed essentially of solvent, if added, catalyst, olefinically unsaturated compound and reaction product. Particularly effective solvents have been found to be the higher-boiling condensation compounds of the aldehydes to be prepared, especially the trimers of the aldehydes to be prepared, which are obtained as by-products in the hydroformylation, and mixtures thereof with the isononanal to be prepared, and so a further addition of solvent is not absolutely necessary. In some cases, however, an addition of solvent may be found to be appropriate. The solvents used are organic compounds in which starting material, reaction product and catalyst are soluble. Examples of such compounds are aromatic hydrocarbons such as benzene and toluene or the isomeric xylenes and mesitylene. Other commonly used solvents are paraffin oil, cyclohexane, n-hexane, n-heptane or n-octane, ethers such as tetrahydrofuran, ketones, or Texanol® from Eastman. The proportion of the solvent in the reaction medium can be varied over a wide range and is typically between 20 and 90% by weight, preferably 50 to 80% by weight, based on the reaction mixture. The hydroformylation of the octene can also be effected without addition of solvent.

The hydroformylation reaction is typically performed in homogeneous organic phase in the presence of at least one transition metal compound of group VIII of the periodic table of the elements. The reaction can be performed either in the presence or in the absence of complex-forming organoelemental compounds which act as complex ligands.

If the hydroformylation reaction is performed in the presence of complex ligands, the use of organophosphorus compounds as organoelemental compounds is suitable. Such complexes and the preparation thereof are known (U.S. Pat. No. 3,527,809 A, U.S. Pat. No. 4,148,830 A, U.S. Pat. No. 4,247,486 A, U.S. Pat. No. 4,283,562 A). They can be used as single complexes. The transition metal concentration in the reaction medium extends over a wide range from about 1 to about 1000 ppm by weight and is preferably 10 to 700 ppm by weight and especially 25 to 500 ppm by weight, based in each case on the homogeneous reaction mixture. The catalyst used may be the transition metal complex of stoichiometric composition. However, it has been found to be appropriate to perform the hydroformylation in the presence of a catalyst system composed of transition metal complex and free complex ligand which does not enter into a complex with the transition metal. The free complex ligand may be the same as in the transition metal complex, but it is also possible to use different complex ligands. The preferred complex ligands include triarylphosphines such as triphenylphosphine, trialkylphosphines such as tri(cyclohexyl) phosphine, alkylphenylphosphines, organic phosphites or diphosphites. The molar ratio of transition metal to complex ligand is generally 1:1 to 1:1000, but it may also be higher. Preference is given to using the transition metal and the complex ligand in a molar ratio of 1:3 to 1:500 and especially of 1:50 to 1:300.

The hydroformylation reaction in the presence of complex ligands is frequently also referred to as the modified variant, which is typically performed at temperatures of 50 to 180° C., preferably of 100 to 160° C. and total pressures of 0.2 to 30 MPa, preferably of 1 to 20 MPa.

The hydroformylation reaction can likewise be performed in the absence of complex ligands according to the unmodified variant. Such transition metal catalysts, for example not modified with phosphines or phosphites, and the suitability thereof as a catalyst for hydroformylation are known from the literature, and they are referred to as unmodified transition metal catalysts. It is assumed in the specialist literature that the transition metal compound $HM(CO)_4$ is the catalytically active transition metal species in the case of unmodified transition metal catalysis, even though this has not been demonstrated clearly owing to the many chemisms which run alongside one another in the reaction zone.

The transition metals of group VIII of the periodic table of the elements used are preferably cobalt, rhodium, iridium, nickel, palladium, platinum, iron or ruthenium, and especially cobalt or rhodium. The modified or unmodified transition metal catalyst forms under the conditions of the hydroformylation reaction from the transition metal compounds used, such as salts thereof, such as chlorides, nitrates, sulphates, acetates, pentanoates, 2-ethylhexanoates or isononanoates, the chalcogenides thereof, such as oxides or sulphides, the carbonyl compounds thereof, such as $M_2(CO)_8$, $M_4(CO)_{12}$, $M_6(CO)_{16}$, $M_2(CO)_9$, $M_3(CO)_{12}$, the organo-transition metal compounds thereof, such as carbonyl acetylacetonates or cyclooctadienyl acetates or chlorides, in the presence of carbon monoxide/hydrogen mixtures. The transition metal compound can be used in solid form or appropriately in solution. Suitable transition metal compounds for use as a catalyst precursor are especially rhodium isononanoate, rhodium acetate, rhodium 2-ethylhexanoate or cobalt isononanoate, cobalt acetate or cobalt 2-ethylhexanoate, or $Co_2(CO)_8$, $Co_4(CO)_{12}$, $Rh_2(CO)_8$, $Rh_4(CO)_{12}$ or $Rh_6(CO)_{16}$ or cyclopentadienyl-rhodium compounds, rhodium acetylacetonate or rhodium dicarbonyl acetylacetonate. Preference is given to using rhodium oxide and especially rhodium acetate, rhodium 2-ethylhexanoate and rhodium isononanoate.

It is also possible first to preform the transition metal catalyst in a precarbonylation stage and then to feed it to the actual hydroformylation stage. The preforming conditions correspond generally to the hydroformylation conditions.

Since the use of transition metal catalysts unmodified with complex ligands generally requires a lower transition metal content, generally an amount of transition metal of 1 to 100 ppm, preferably 2 to 30 ppm, based on the octene used, is employed. Very particularly, rhodium or cobalt is used in an amount of 2 to 30 ppm, preferably of 5 to 10 ppm, based in each case on the octene used.

In the reaction of octene with hydrogen and carbon monoxide to give isononanal by the unmodified variant, appropriately relatively high pressures in the range from 5 to 70 MPa, preferably from 5 to 60 MPa and especially from 10 to 30 MPa are employed. Suitable reaction temperatures vary within the range from 50 to 180° C., preferably from 50 to 150° C. and especially 100 to 150° C.

The composition of the synthesis gas, i.e. the proportions of carbon monoxide and hydrogen in the gas mixture, may vary within wide limits. In general, mixtures in which the molar ratio of carbon monoxide to hydrogen is 5:1 to 1:5 are used. Typically, this ratio is 1:1 or differs only slightly from this value. The olefinic compound can be supplied to the reaction zone as such or in solution. Suitable solvents are ketones such as acetone, methyl ethyl ketone, acetophenone, lower aliphatic nitriles such as acetonitrile, propionitrile or benzonitrile, dimethylformamide, linear or branched saturated aliphatic monohydroxyl compounds such as methanol, ethanol, propanol and isopropanol, aromatic hydrocarbons such as benzene or toluene, and saturated cycloaliphatic hydrocarbons such as cyclopentane or cyclohexane.

The hydroformylation stage can be performed either batchwise or continuously. The desired aldehydes are obtained from the crude hydroformylation product by conventional processes, for example by distillation. Isononanal and further volatile components are drawn off as top products and subjected to further fine purification if required.

The amounts of transition metal used are obtained in the distillation residue and, optionally after addition of fresh transition metal compound and withdrawal of a portion of the aldehyde condensation products formed in the course of the reaction, are recycled into the reaction zone.

The resulting mixture of isomeric isononanals is purified, appropriately by distillation, and then converted by oxidation to the corresponding isononanoic acid, preferably by the oxidation in the liquid phase, although other process configurations such as oxidation in the gas phase are not ruled out. Suitable oxidizing agents are customary compounds suitable for oxidation of aliphatic aldehydes, such as oxygen, oxygen-containing gas mixtures, ozone, ozone-containing gas mixtures, peroxides, peracids, metal salts of peracids or transition metals in high oxidation states, for example potassium permanganate or manganese dioxide. Owing to good availability, the oxidizing agents used are appropriately molecular oxygen or gas mixtures comprising molecular oxygen. Further constituents of such gas mixtures are inert gases, for example nitrogen, noble gases and carbon dioxide. The proportion of the inert constituents of the oxygen-containing gas mixture is up to 90% by volume, especially 30 to 80% by volume. The preferred oxidizing agents are oxygen or air.

The oxidation can be performed either with addition of catalysts or in the absence of catalysts. Suitable catalysts are transition metals or compounds of transition metals which can be added in small amounts, for example from 0.1 to 5 ppm, calculated as the transition metal and based on the aldehyde used, such as titanium, vanadium, chromium, molybdenum, manganese, iron, cobalt, nickel, ruthenium, rhodium, palladium or copper. Such a process regime is described, for example, in DE 100 10 771 C1 or DE 26 04 545 A1.

It is likewise possible to perform the conversion in the presence of alkali metal or alkaline earth metal salts of weak acids. Especially in the case of oxidation of α-branched aldehydes in which the carbon atom adjacent to the carbonyl carbon atom bears the branch, the prior art recommends the presence of small amounts of alkali metal carboxylates to improve selectivity (DE 950 007, DE 100 10 771 C1). It is also possible to use a combination of alkali metal or alkaline earth metal carboxylates with transition metal compounds, as discussed in EP 1 854 778 A1.

In the oxidation of isononanal, which is prepared by the process according to the invention proceeding from 2-ethylhexanol via the dehydration and hydroformylation of the corresponding octene, the presence of alkali metal or alkaline earth metal carboxylates is advisable, generally in an amount of 1 to 30 mmol, preferably of 1 to 15 mmol and especially of 1 to 8 mmol per mole of aldehyde, calculated as the alkali metal or alkaline earth metal.

It is not necessary to use the alkali metal or alkaline earth metal carboxylates as a single compound. It is likewise possible to use mixtures of these compounds, although it is appropriate to use isononanoates. Preference is given, however, to using single compounds, for example lithium isononanoate, potassium isononanoate, sodium isononanoate, calcium isononanoate or barium isononanoate.

In general, a solution comprising alkali metal or alkaline earth metal isononanoates is prepared by neutralizing an aqueous solution comprising the alkali metal or alkaline earth metal compound with an excess of isononanoic acid, and this solution is added to the isononanal to be oxidized. Suitable alkali metal or alkaline earth metal compounds are particularly the hydroxides, carbonates or hydrogencarbonates.

However, it is also possible to obtain the alkali metal or alkaline earth metal isononanoates in the reaction mixture by adding alkali metal or alkaline earth metal compounds which are converted to the isononanoates under the reaction conditions. For example, it is possible to use alkali metal or alkaline earth metal hydroxides, carbonates, hydrogencarbonates or oxides in the oxidation stage. They can be added either in solid form or as an aqueous solution.

The reaction with the oxidizing agent, preferably with oxygen or oxygen-containing gases, is conducted within a temperature range from 20 to 100° C. Preference is given to working between 20 and 80° C., especially between 40 and 80° C. The temperature regime, constant or variable temperature, can be adapted to the individual requirements of the starting material and the reaction conditions.

The conversion of the reactants is preferably effected under atmospheric pressure. However, the use of elevated pressure is not ruled out. It is customary to work within a range from atmospheric pressure to 1.5 MPa, preferably at atmospheric pressure to 0.8 MPa.

The reaction time required for conversion of the isononanal to the corresponding isononanoic acid depends upon factors including the reaction temperature and the ratio of the reactants to one another. It is normally 30 minutes to 20 hours, especially 2 to 8 hours.

Isononanal can be used as such or dissolved in a solvent which is inert under the reaction conditions. Examples of suitable solvents are ketones such as acetone, esters, for example ethyl acetate, hydrocarbons, for example toluene, and nitrohydrocarbons such as nitrobenzene. The concentration of the aldehyde is limited by the solubility thereof in the solvent.

The oxidation step can be performed batchwise or continuously. Recycling of unconverted reaction participants is possible in both cases.

The isononanoic acid obtained proceeding from 2-ethylhexanol is a mixture of positionally isomeric aliphatic C9 monocarboxylic acids with α-unbranched and singly branched isononanoic acids as main components.

According to the gas chromatography analysis to DIN 51405 (area %), the main components present are 4-methyloctanoic acid, 6-methyloctanoic acid, 2,5-dimethylheptanoic acid, 2,3-dimethylheptanoic acid, 3-ethylheptanoic acid, 2-ethylheptanoic acid and 2-ethyl-4-methylhexanoic acid, and also small amounts of 2-propyl-3-methylpentanoic acid and 2-methyloctanoic acid. Small amounts of n-nonanoic acid are likewise present.

The isononanoic acid prepared by the process according to the invention is characterized in that the main components 4-methyloctanoic acid, 6-methyloctanoic acid, 2,5-dimethylheptanoic acid, 2,3-dimethylheptanoic acid, 3-ethylheptanoic acid, 2-ethylheptanoic acid and 2-ethyl-4-methylhexanoic acid make up a total amount of at least 80 mol %, based on the total content of positionally isomeric aliphatic C9-monocarboxylic acids.

From the crude acid mixture obtained after the oxidation, the pure isononanoic acid is obtained by means of distillation under customary conditions. The distillation residue containing the alkali metal or alkaline earth metal isononanoates and possibly transition metals is removed and can be fed back to the input aldehyde, optionally after addition of fresh alkali metal or alkaline earth metal isononanoates or alkali metal or alkaline earth metal compounds which are converted to the isononanoates under the reaction conditions, and optionally of fresh transition metal compounds.

In a proven embodiment of the process according to the invention, isononanal is initially charged in a suitable reactor, for example in a tubular reactor which has been provided with an inflow tray and optionally also contains random packings, and the oxygen or the oxygen-containing gas mixture is passed through the aldehyde from the bottom.

According to a further embodiment, the reactor used is a trickle tower containing random packings. The aldehyde is allowed to trickle downwards through the packing, and oxygen or an oxygen-containing gas mixture is simultaneously introduced into the tower in cocurrent or countercurrent.

The isononanoic acid prepared by the process according to the invention can be used, for example, by processes known per se for preparation of derivatives such as the vinyl ester, carboxylic esters, isononanoic anhydrides, isononanoyl halides or isononanamides. The vinyl ester is prepared, for example, by reaction of isononanoic acid with acetylene, preferably in the presence of zinc salts at temperatures of 200-230° C. (G. Hübner, Fette, Seifen, Anstrichmittel 68, 290 (1966), Ullmann's Encyclopedia of Industrial Chemistry, 7th Edition, 2011, Wiley, Volume 38, pages 107-124) or by what is called the transvinylation reaction

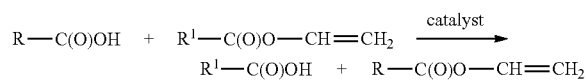

where R is C8 and $R^1$ is frequently methyl or ethyl, and so the transvinylation reagent used is, for example, vinyl acetate or vinyl propionate (Ullmann's Encyclopedia of Industrial Chemistry, 7th Edition, 2011, Wiley, Volume 38, pages 107-124). In order to force the chemical equilibrium in the direction of the desired vinyl ester, an excess of the transvinylation reagent $R^1$—C(O)—CH=CH$_2$ is frequently used, and the carboxylic acid formed is simultaneously removed from the reaction mixture. Suitable transvinylation catalysts are compounds of the transition metals from the platinum group ruthenium, osmium, rhodium, iridium, palladium and platinum, especially palladium and ruthenium, which can be used modified with mono- or polydentate organonitrogen or organophosphorus ligands or in unmodified form.

The resulting vinyl isononanoate is suitable as a comonomer in polyvinyl acetate, polyvinyl chloride, polystyrene or polyacrylic esters, which has an advantageous effect on the hydrolysis stability and moisture absorption of paints.

The isononanoic acid prepared in accordance with the invention can likewise be used to prepare the corresponding glycidyl ester, for example by reaction with epichlorohydrin, by processes known per se, and this can serve for modification of alkyd resins (Weissermel, Arpe, Industrielle Organische Chemie, VCH Verlagsgesellschaft, 3rd Edition, 1988, page 152; U.S. Pat. No. 6,433,217).

The isononanoic acid prepared in accordance with the invention can likewise be reacted with mono- or polyhydric alcohols in a manner known per se to give the corresponding carboxylic esters (Ullmanns Encyklopädie der technischen Chemie, 4th Edition, 1976, Verlag Chemie, Volume 11, pages 89-96), which can be used in lubricant compositions, as a plasticizer for thermoplastic polymers or as a coalescence agent in emulsion paints.

It is likewise possible to derivatize the isononanoic acid prepared in accordance with the invention by reaction with halogenating agents such as phosphorus pentachloride, phosphorus oxychloride, sulphuryl chloride or thionyl chloride to isononanoyl halides, from which isononanoic anhydride is obtainable by reaction with isononanoic acid or mixed anhydrides are obtainable by reaction with other carboxylic acids. The reaction of isononanoic acid with acetic anhydride also gives, as an intermediate, the mixed anhydride, which can be converted with further addition of acid and acetic acid elimination to isononanoic anhydride or to a further mixed anhydride (Ullmanns Encyklopädie der technischen Chemie, 4th Edition, 1975, Verlag Chemie, Volume 9, pages 145-146). Proceeding from isononanoyl chloride or isononanoic anhydride, by reaction with ammonia, primary or secondary amines, it is possible to obtain the corresponding isononanamides (Methoden der Organischen Chemie, Houben-Weyl, 4th Edition, 1958, Georg Thieme Verlag, Stuttgart, Volume XI/2, pages 10-14, 16-19).

The examples which follow describe the preparation of isononanoic acid proceeding from 2-ethylhexanol.

EXAMPLES

I. Dehydration of 2-ethylhexanol

For dehydration, a quartz tube having a length of 1.3 meters and a diameter of 0.03 meter was used, in which the heated zone extended over 1.1 meters. The quartz tube was charged with 250 ml of the acidic catalyst AI 3996 from BASF SE in the form of tablets of size 3×3 millimeters. The dead volume was filled with glass rings.

2-Ethylhexanol was evaporated in an upstream evaporator and conducted with the aid of a nitrogen stream as carrier gas at standard pressure over the catalyst bed at a temperature of 350° C. and with a space velocity of 0.5 liter per liter of catalyst volume and hour. The reaction mixture obtained was condensed in a downstream collecting vessel and the aqueous phase was removed. The organic phase obtained had the following composition determined by gas chromatography (area %, to DIN 51405):

| | |
|---|---|
| Forerun/C4-C7 hydrocarbons | 0.3 |
| Other C8 olefins | 9.6 |
| 2-ethyl-1-hexene | 7.6 |
| cis-3-methyl-3-heptene | 14.6 |
| trans-3-methyl-3-heptene | 28.8 |
| cis-3-methyl-2-heptene | 16.2 |
| trans-3-methyl-2-heptene | 23.9 |
| n-octenes | 0.8 |
| Final fraction | 0.1 |

II. Hydroformylation of the Octene Obtained in Step I

The crude octene obtained in step I was hydroformylated in the presence of 5 ppm of rhodium, added in the form of a solution of rhodium 2-ethylhexanoate in 2-ethylhexanol and based on octene input, at a temperature of 140° C. and a synthesis gas pressure of 19 MPa over a period of three hours. The molar composition of the synthesis gas was 1 mol of hydrogen to 1 mol of carbon monoxide. The crude hydroformylation product obtained had the following composition determined by gas chromatography (area %, to DIN 51405):

| | |
|---|---|
| Forerun | 0.1 |
| C8 hydrocarbons | 8.5 |
| Intermediate fraction | 0.2 |
| Isononanal | 88.1 |
| n-nonanal | 1.4 |
| Final fraction | 1.7 |

The results of further hydroformylation experiments with octene obtained via the dehydration of 2-ethylhexanol are compiled in Table 1 below. Before use, the crude octene was distilled in a Claise bridge to remove the final fraction at a top temperature of 119-122° C. and at standard pressure. The input octenes and the reaction products obtained were analysed by gas chromatography (figures in area %, to DIN 51405).

TABLE 1

Hydroformylation of octenes obtained by 2-ethylhexanol dehydration

| | Example | |
|---|---|---|
| | IIa | IIb |
| Reactant input | distilled | distilled |
| GC analysis of reactant (%) | | |
| Forerun/C4-C7 hydrocarbons | 0.3 | 0.4 |
| Other C8 olefins | 5.9 | 7.7 |
| 2-ethyl-1-hexene | 9.3 | 9.2 |
| cis-3-methyl-3-heptene | 15.2 | 15.0 |
| trans-3-methyl-3-heptene | 27.4 | 27.1 |
| cis-3-methyl-2-heptene | 16.1 | 15.6 |
| trans-3-methyl-2-heptene | 25.2 | 24.7 |
| n-octenes | 0.5 | 0.2 |
| Final fraction | 0.1 | 0.1 |
| Experimental conditions | | |
| Rh concentration [ppm], based on octene input | 20 | 10 |
| Pressure [MPa] | 19 | 27 |
| Temperature [° C.] | 140 | 140 |
| Reaction time [h] | 2 | 2 |
| GC analysis of product (%) | | |
| Forerun | 0.1 | 0.1 |
| C8 hydrocarbons | 2.5 | 1.1 |
| Intermediate fraction | 0.3 | 0.1 |
| isononanals | 90.8 | 94.7 |
| n-nonanal | 2.0 | 1.4 |
| Final fraction | 4.3 | 2.6 |

The hydroformylation experiments conducted using triphenylphosphine as complex ligand with the octene obtained via the dehydration of 2-ethylhexanol are compiled in Table 2 below. Undistilled material was used. The input octenes and the reaction products obtained were analysed by gas chromatography (figures in area %, to DIN 51405).

TABLE 2

Hydroformylation of octenes, obtained by the 2-ethylhexanol dehydration, addition of triphenylphosphine

| Example | IIc | IId | IIe | IIf |
|---|---|---|---|---|
| Reactant input | un-distilled, crude | un-distilled, crude | un-distilled, crude | un-distilled, crude |
| GC analysis of reactant (%) | | | | |
| C4-C7 hydrocarbons | 0.3 | 0.3 | 0.3 | 0.4 |
| Other C8 olefins | 19.1 | 19.1 | 19.1 | 11.6 |
| 2-ethyl-1-hexene | 7.9 | 7.9 | 7.9 | 8.6 |
| 3-methyl-3-heptene | 36.5 | 36.5 | 36.5 | 40.0 |
| 3-methyl-2-heptene | 36.2 | 36.2 | 36.2 | 39.3 |
| Final fraction | <0.01 | <0.01 | <0.01 | <0.1 |
| Experimental conditions | | | | |
| Rh concentration [ppm], based on octene input | 10 | 10 | 10 | 10 |
| Equivalents of TPP | 3 | 50 | 100 | 3 |
| Pressure [MPa] | 18 | 27 | 18 | 14 |
| Temperature [° C.] | 140 | 140 | 140 | 160 |
| Reaction time [h] | 1 | 2 | 1 | 2 |
| GC analysis of product (%) | | | | |
| Forerun | 0.1 | 0.1 | 0.1 | 0.1 |
| C8 hydrocarbons | 52.2 | 70.9 | 81.7 | 14.1 |
| Intermediate fraction | 0.8 | 0.1 | 0.1 | 1.9 |
| isononanals | 45.7 | 28.3 | 17.6 | 76.1 |
| n-nonanal | 0.5 | 0.1 | 0.1 | 0.5 |
| Final fraction | 0.7 | 0.4 | 0.4 | 7.3 |

III. Oxidation of the Isononanal Obtained in Step II. To Isononanoic Acid

From the isononanal obtained in Example IIa, low boilers and unconverted olefin as the top product were first removed in a 24-tray column at 200 hPa, a bottom temperature of 120° C. and a reflux ratio of 2:1. After low boiler removal, the bottom temperature was raised to 140-150° C. and the isononanal was drawn off overhead (boiling point at 100 hPa: 110-114° C.), while high boilers remained in the distillation bottoms.

The isononanal obtained had the composition determined by gas chromatography which follows and the parameters which follow, and was used for the subsequent liquid phase oxidation.

TABLE 3

Gas chromatography analysis (area %, to DIN 51405) of isononanal proceeding from 2-ethylhexanol

| | |
|---|---|
| Forerun/C8 hydrocarbons | 0.2 |
| Intermediate fraction | 0.4 |
| 2-ethyl-4-methylhexanal | 10.8 |
| 2-propyl-3-methylpentanal | 3.6 |
| 2,5-dimethylheptanal | 21.9 |
| 2,3-dimethylheptanal (isomer) | 4.8 |
| 2,3-dimethylheptanal (isomer) + 2-ethylheptanal | 8.4 |
| 2-methyloctanal | 1.7 |
| 3-ethylheptanal | 10.4 |
| 4-methyloctanal | 20.6 |
| 4,5-dimethylheptanal | 0.6 |
| 6-methyloctanal | 11.0 |
| Other i-nonanals | 1.8 |
| n-nonanal | 0.9 |
| Final fraction | 2.9 |

TABLE 4

Parameters of the isononanal proceeding from 2-ethylhexanol

| Parameter/unit | DIN/ASTM | Value |
|---|---|---|
| $V_{20}$ (mm$^2$/s) | ASTM D 445 | 1.536 |
| $V_{40}$ (mm$^2$/s) | | 1.179 |
| Solidification point (° C.) | | −100 |
| $d^{20/4}$ (g/cm$^3$) | DIN 51757, | 0.827 |
| $d^{50/4}$ (g/cm$^3$) | Method D/ASTM D 4052 | 0.811 |
| $n^{20/D}$ | DIN 51423-2/ ASTM D 1747 | 1.424 |
| CO number (mg KOH/g) | DIN 53173 | 339/349 |
| Flashpoint (° C.) | DIN EN ISO 2719 | 60 |
| Platinum/cobalt Hazen colour number | DIN EN ISO 6271/ ASTM D 1209 | 15 |

The liquid phase oxidation of the isononanal to isononanoic acid was effected without addition of solvent in a bubble column reactor at 50° C. with pure oxygen at standard pressure over a period of 6 hours. A 50% by weight aqueous solution of potassium hydroxide was added to the input aldehyde in such an amount that 50 mmol of potassium were present per mole of isononanal.

The crude acid obtained was subsequently distilled in a 4.5-tray column at a bottom temperature of 148 to 159° C. and at a top temperature of 136-139° C. at 20 hPa. Low boilers and unconverted aldehyde were removed as the forerun fraction, and high boilers remained in the distillation residue. The distillation yield of isononanoic acid was 84.7% with a purity determined by gas chromatography of 98.8%.

The resulting isononanoic acid had the following composition determined by gas chromatography to DIN 51405 (area %):

TABLE 5

Gas chromatography analysis of the isononanoic acid proceeding from 2-ethylhexanol (area %, to DIN 51405)

| | |
|---|---|
| Forerun | 0.4 |
| 2-ethyl-4-methylhexanoic acid | 9.3 |
| 2-propyl-3-methylpentanoic acid | 3.0 |
| 2,5-dimethylheptanoic acid + 2,3-dimethylheptanoic acid (isomer) | 25.7 |
| 2,3-dimethylheptanoic acid (isomer) | 8.4 |
| 3-ethylheptanoic acid + 2-ethylheptanoic acid | 12.9 |
| 2-methyloctanoic acid | 0.8 |
| 4-methyloctanoic acid | 20.9 |
| 6-methyloctanoic acid | 12.3 |
| n-nonanoic acid | 0.3 |
| Other i-nonanoic acids | 5.2 |
| Final fraction | 0.8 |

The parameters determined for the isononanoic acid are compiled in Table 6.

TABLE 6

Parameters of isononanoic acid proceeding from 2-ethylhexanol

| Parameter/unit | DIN/ASTM | Value |
|---|---|---|
| $V_{20}$ (mm$^2$/s) | ASTM D 445 | 10.68-11.18 |
| $V_{40}$ (mm$^2$/s) | | 5.83-5.88 |
| $V_{50}$ (mm$^2$/s) | | 4.50 |
| $d^{20/4}$ (g/cm$^3$) | DIN 51757, Method D/ | 0.906-0.907 |
| $d^{40/4}$ (g/cm$^3$) | | 0.891 |
| $d^{50/4}$ (g/cm$^3$) | ASTM D 4052 | 0.883-0.884 |
| $n^{20/D}$ | DIN 51 423-2/ ASTM D 1747 | 1.432-1.433 |
| Solidification point (° C.) | | −81 |
| Boiling point (° C.) at 1013 hPa | DIN 53171/ ASTM D 1078 | 241-242 |
| Acid number (mg KOH/g) | DIN EN ISO 2114/ ASTM D 1613 | 351 |
| Flashpoint (° C.) | DIN EN ISO 2719 | 129 |
| Platinum/cobalt Hazen colour number | DIN EN ISO 6271/ ASTM D 1209 | 7 |

The invention claimed is:

1. A process for preparing isononanoic acid proceeding from 2-ethylhexanol, wherein
 (a) 2-ethylhexanol is dehydrated to octene in the presence of a catalyst;
 (b) the octene obtained in step a) is reacted in the presence of a transition metal compound of group VIII of the periodic table of the elements with carbon monoxide and hydrogen to give isononanal; and
 c) the isononanal obtained in step b) is oxidized to isononanoic acid.

2. The process according to claim 1, wherein the catalyst used in step a) is alumina, nickel precipitated on alumina, or phosphoric acid precipitated on silica or alumina.

3. The process according to claim 1, wherein 2-ethylhexanol is dehydrated in the gas phase in step a).

4. The process according to claim 1, wherein the transition metal compound of group VIII of the periodic table of the elements used in step b) is a cobalt or rhodium compound.

5. The process according to claim 1, wherein the reaction in step b) is performed in the absence of complex-forming organophosphorous compounds.

6. The process according to claim 1, wherein the isononanal obtained in step b) is distilled.

7. The process according to claim 1, wherein the oxidation in step c) is effected in the presence of alkali metal or alkaline earth metal carboxylates.

8. The process according to claim 7, characterized in that wherein the alkali metal or alkaline earth metal carboxylate used is lithium isononanoate, potassium isononanoate, sodium isononanoate, calcium isononanoate or barium isononanoate.

9. The process according to claim 1, wherein isononanal is oxidized in the liquid phase in step c).

10. The process according to claim 1, wherein isononanal is oxidized in step c) with oxygen or oxygen-containing gases to provide isononanoic acid.

11. The process for preparing vinyl isononanoate, wherein the isononanoic acid according to claim 1 is reacted with acetylene.

12. The process for preparing vinyl isononanoate, wherein the isononanoic acid according to claim 1 is reacted with vinyl acetate or vinyl propionate.

13. The process for preparing carboxylic esters, wherein the isononanoic acid according to claim 1 is esterified with mono- or polyhydric alcohols.

14. The process for preparing isononanoyl halides, wherein the isononanoic acid according to claim 1 is reacted with halogenating agents.

15. The process for preparing isononanoic anhydrides, wherein the isononanoic acid according to claim 1 is reacted with halogenating agents and then with carboxylic acids.

16. The process for preparing isononanamides, characterized in wherein the isononanoic acid according to claim 1 is converted to isononanoyl chloride or isononanoic anhydride and then reacted with ammonia, primary or secondary amines.

17. The process for preparing the glycidyl ester of isononanoic acid, wherein the isononanoic acid according to claim 1 is converted to the glycidyl ester.

18. The process according to claim 2, 2-ethylhexanol is dehydrated in the gas phase in step a).

19. The process according to claim 2, wherein the transition metal compound of group VIII of the periodic table of the elements used in step b) is a cobalt or rhodium compound.

* * * * *